United States Patent
Im et al.

(10) Patent No.: US 10,471,416 B2
(45) Date of Patent: Nov. 12, 2019

(54) METHOD FOR OLIGOMERIZING AN OLEFIN

(71) Applicant: LG CHEM, LTD., Seoul (KR)

(72) Inventors: Seul Ki Im, Daejeon (KR); Yong Ho Lee, Daejeon (KR); Eun Ji Shin, Daejeon (KR); Jin Young Park, Daejeon (KR); Seok Pil Sa, Daejeon (KR); Ki Soo Lee, Daejeon (KR)

(73) Assignee: LG CHEM, LTD., Seoul (KR)

(*) Notice: Subject to any disclaimer, the term of this patent is extended or adjusted under 35 U.S.C. 154(b) by 64 days.

(21) Appl. No.: 15/529,385

(22) PCT Filed: Feb. 2, 2016

(86) PCT No.: PCT/KR2016/001150
§ 371 (c)(1),
(2) Date: May 24, 2017

(87) PCT Pub. No.: WO2016/129848
PCT Pub. Date: Aug. 18, 2016

(65) Prior Publication Data
US 2017/0267603 A1 Sep. 21, 2017

(30) Foreign Application Priority Data

Feb. 12, 2015 (KR) .................. 10-2015-0021784
Sep. 3, 2015 (KR) .................. 10-2015-0125097

(51) Int. Cl.
| | | |
|---|---|---|
| *C07C 2/24* | (2006.01) | |
| *B01J 31/24* | (2006.01) | |
| *B01J 31/02* | (2006.01) | |
| *B01J 31/04* | (2006.01) | |
| *B01J 31/14* | (2006.01) | |
| *C07C 2/32* | (2006.01) | |
| *C08F 210/16* | (2006.01) | |
| *C08F 2/40* | (2006.01) | |
| *C08F 4/69* | (2006.01) | |
| *C08F 10/00* | (2006.01) | |
| *C08K 5/05* | (2006.01) | |
| *B01J 31/18* | (2006.01) | |
| *C07F 9/50* | (2006.01) | |
| *B01J 35/00* | (2006.01) | |
| *B01J 37/04* | (2006.01) | |
| *C08F 10/02* | (2006.01) | |

(52) U.S. Cl.
CPC ....... *B01J 31/2409* (2013.01); *B01J 31/0267* (2013.01); *B01J 31/04* (2013.01); *B01J 31/143* (2013.01); *B01J 31/187* (2013.01); *B01J 31/188* (2013.01); *B01J 35/0006* (2013.01); *B01J 37/04* (2013.01); *C07C 2/24* (2013.01); *C07C 2/32* (2013.01); *C07F 9/505* (2013.01); *C07F 9/5022* (2013.01); *C08F 2/40* (2013.01); *C08F 4/69* (2013.01); *C08F 10/00* (2013.01); *C08F 10/02* (2013.01); *C08F 210/16* (2013.01); *C08K 5/05* (2013.01); *B01J 2231/12* (2013.01); *B01J 2231/20* (2013.01); *B01J 2523/67* (2013.01); *B01J 2531/004* (2013.01); *B01J 2531/31* (2013.01); *B01J 2531/62* (2013.01); *C07C 2523/26* (2013.01); *C07C 2531/04* (2013.01); *C07C 2531/14* (2013.01); *C07C 2531/18* (2013.01); *C07C 2531/22* (2013.01); *C07C 2531/24* (2013.01)

(58) Field of Classification Search
CPC .. C07C 2/32; C07C 2/36; C07C 11/02; C07C 11/107; C07C 2/12; C07C 2531/24; C07C 2529/70; C07C 2531/14; C07C 2529/40; C07C 2531/18; C07C 2531/34; B01J 31/143; B01J 31/189; B01J 29/041; B01J 29/06; B01J 29/40; B01J 29/7007; B01J 29/7042; B01J 31/188; B01J 31/1885; B01J 31/2495; B01J 35/023; B01J 37/0009; B01J 37/0045
USPC .................................................. 585/502, 513
See application file for complete search history.

(56) References Cited

U.S. PATENT DOCUMENTS

| | | | |
|---|---|---|---|
| 2005/0049448 A1* | 3/2005 | Loescher ............... | C07C 11/02 585/533 |
| 2006/0247483 A1 | 11/2006 | McConville et al. | |

(Continued)

FOREIGN PATENT DOCUMENTS

| | | | |
|---|---|---|---|
| JP | 2008533030 A | 8/2008 | |
| JP | 2009516672 A | 4/2009 | |

(Continued)

OTHER PUBLICATIONS

Jiang, T. et. al. "The effect of N-aryl bisphosphine ligands on the selective ethylene tetramerization", J. Mol. Catal. A (2008), 279, pp. 90-93. (Year: 2008).*

(Continued)

Primary Examiner — Sharon Pregler
(74) Attorney, Agent, or Firm — Dentons US LLP

(57) ABSTRACT

A method for oligomerizing an olefin comprising performing a multimerization reaction of an olefin in the presence of an oligomerization catalyst system comprising a ligand compound, a transition metal compound and a co-catalyst, and controlling a reaction temperature during the multimerization reaction in a range of 30 to 150° C., such that a product of the multimerization reaction comprising 1-hexene and 1-octene has a predetermined value of a weight ratio of 1-hexene and 1-octene selected from a range of 1:0.5 to 1:7.

16 Claims, No Drawings

(56) References Cited

U.S. PATENT DOCUMENTS

| | | |
|---|---|---|
| 2007/0161503 A1 | 7/2007 | Briggs et al. |
| 2007/0185357 A1 | 8/2007 | De Boer et al. |
| 2008/0027188 A1* | 1/2008 | Small .................. B01J 31/143 526/113 |
| 2008/0207857 A1 | 8/2008 | Small et al. |
| 2008/0293899 A1 | 11/2008 | McConville et al. |
| 2010/0137669 A1 | 6/2010 | Han et al. |
| 2011/0172482 A1* | 7/2011 | Cabiac .................. B01J 29/041 585/502 |
| 2012/0116141 A1* | 5/2012 | Godsmark ................ C07C 2/12 585/533 |
| 2012/0172645 A1* | 7/2012 | Sydora .................. B01J 31/143 585/511 |
| 2014/0081064 A1 | 3/2014 | Han et al. |
| 2014/0179970 A1* | 6/2014 | Fritz .................. B01J 31/143 585/513 |
| 2015/0011382 A1 | 1/2015 | Kwon et al. |
| 2015/0018502 A1 | 1/2015 | Kwon et al. |
| 2015/0298110 A1 | 10/2015 | Cho et al. |
| 2016/0083311 A1† | 3/2016 | Maumela |
| 2018/0016206 A1 | 1/2018 | Han et al. |

FOREIGN PATENT DOCUMENTS

| | | |
|---|---|---|
| JP | 2010526647 A | 8/2010 |
| KR | 1020130126517 A | 11/2013 |
| KR | 1020130142151 A | 12/2013 |
| KR | 1020140063346 A | 5/2014 |
| WO | 2006096881 A1 | 9/2006 |
| WO | 2015/015402 A2 | 2/2015 |

OTHER PUBLICATIONS

Killian, E. et. al. "The use of bis(diphenylphosphino)amines with N-aryl functionalities in selective ethylene tri- and tetramerization", J. Mol. Catal. A (2007), 270, pp. 214-218. (Year: 2007).*

Anthea Carter et al., High activity ethylene trimerisation catalysts based on diphosphine ligands, Chemical Communications, 2002, vol. 8, pp. 858-859.

Sven Kuhlmann, et al.: "Influence of Elevated Temperature and Pressure on the Chromium-Catalysed Tetramerisation of Ethylene", XP055438670, Advanced Synthesis & Catalysis, vol. 348, No. 10-11, Jul. 1, 2006, pp. 1200-1206.

\* cited by examiner
† cited by third party

METHOD FOR OLIGOMERIZING AN OLEFIN

CROSS-REFERENCE TO RELATED APPLICATIONS

This application is a National Stage Application of International Application No. PCT/KR2016/001150, filed Feb. 2, 2016, and claims the benefit of Korean Patent Application No. 10-2015-0021784, filed Feb. 12, 2015, and Korean Patent Application No. 10-2015-0125097, filed Sep. 3, 2015, contents of which are incorporated herein by reference in their entirety for all purposes as if fully set forth below.

TECHNICAL FIELD

The present invention relates to a method for oligomerizing an olefin capable of controlling the production ratio of 1-hexene and 1-octene by controlling the reaction temperature of the olefin multimerization.

BACKGROUND ART

Linear alpha-olefins are important materials used as comonomers, cleaners, lubricants, plasticizers, etc. and are commercially and widely used. Particularly, 1-hexene and 1-octene are widely used as comonomers for controlling the density of polyethylene during the preparation of linear low-density polyethylene (LLDPE).

In a preparation process of common LLDPE, copolymerization of alpha-olefins, for example, 1-hexene, 1-octene, etc. with ethylene is performed to control density by forming branches on a polymer backbone.

Accordingly, in the preparation of LLDPE having a high comonomer content, the comonomer is a costly part. To solve the drawback, various methods have been conducted.

In addition, the application field or the market size of alpha-olefins is dependent on the kind thereof, and technique on selective production of a specific olefin is commercially very important. Recently, research on a technique using a chromium catalyst for preparing 1-hexene or 1-octene with high selectivity via selective ethylene oligomerization is being actively conducted.

Conventional and commercial preparation methods of 1-hexene or 1-octene include the Shell higher olefin process (SHOP) of Shell Chemicals, the Ziegler process of Chevron Philips Chemical, etc. Through the methods, alpha-olefins having a wide distribution of C4-C20 may be obtained.

As a catalyst for trimerizing ethylene, a chromium-based catalyst using a ligand having a formula of (R1)(R2)X—Y—X(R3)(R4) is suggested. In the formula, X is phosphorus, arsenic or antimony, Y is a linking group such as —N(R5)-, and at least one of R1, R2, R3 and R4 have a polar or electron donating substituent.

In addition, a compound of (o-ethylphenyl)2PN(Me)P(o-ethylphenyl)2 comprising no polar substituent for at least one of R1, R2, R3 and R4 has been studied as a ligand not exhibiting catalyst activity to 1-hexene under catalytic conditions (*Chem. Commun.*, 2002, 858).

However, the conventional ligand comprising a heteroatom is still required to have consistent and continuous activity on multimerization reaction and high selectivity during preparing 1-octene or 1-hexene.

PRIOR ARTS

Non-Patent Document

*Chem. Commun.*, 2002, 858

DISCLOSURE OF THE INVENTION

Technical Problem

In the present disclosure, there is provided a method for oligomerizing an olefin, in which 1-hexene and 1-octene may be produced in a predetermined production ratio by controlling the reaction temperature during the multimerization reaction of the olefin.

Technical Solution

According to an aspect of the present invention, there is provided a method for oligomerizing an olefin comprising performing a multimerization reaction of an olefin in the presence of an oligomerization catalyst system comprising a ligand compound, a transition metal compound and a co-catalyst by controlling a reaction temperature in a range of 30 to 150° C., so that a weight ratio of 1-hexene and 1-octene in a product comprising 1-hexene and 1-octene has a predetermined value, wherein the predetermined value of the weight ratio of 1-hexene to 1-octene in the product is selected from a range of 1:0.5 to 1:7.

In an embodiment, the predetermined value of the weight ratio may be from 1:0.9 to 1:6.6.

In an embodiment, a ratio of 1-hexene in the product may increase according to the increase of the reaction temperature.

In an embodiment, the reaction temperature may be controlled in a range of 60 to 130° C.

In an embodiment, a selectivity of 1-hexene and 1-octene relative to a total amount of the product may be 80 wt % or more in a whole reaction temperature range.

In an embodiment, an activity decreasing ratio of a catalyst system according to an increase of temperature may be less than 6% in a whole reaction temperature range.

In an embodiment, an activity of a catalyst system in a whole reaction temperature range may be 100,000 kg/molCr/hr or more in a batch type process, and 100,000 kg/molCr or more in a continuous type process.

In an embodiment, the ligand compound may comprise a diphosphine moiety represented by the following Formula 1.

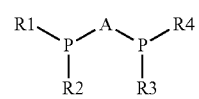

[Formula 1]

In Formula 1, A is N, As or Sb, R1 to R4 are each independently hydrocarbyl, heterohydrocarbyl or hydrocarbylheteryl having 1 to 20 carbon atoms.

In an embodiment, the ligand compound may comprise at least two diphosphine moieties represented by the following Formula 2, and a linker connecting the at least two diphosphine moieties may be hydrocarbyl, and a carbon number in the shortest distance between the diphosphine moieties may be from 2 to 30.

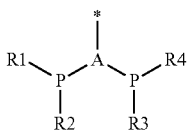

[Formula 2]

In Formula 2, A and R1 to R4 are the same as defined in Formula 1, and * is a linker connecting at least two diphosphine moieties.

In an embodiment, the linker may be combined with at least one group selected from the group consisting of an aliphatic group having 1 to 20 carbon atoms, a heteroaliphatic group having 2 to 20 carbon atoms, an alicyclic group having 3 to 20 carbon atoms, a heteroalicyclic group having 3 to 20 carbon atoms, an aromatic group having 6 to 20 carbon atoms, and a heteroaromatic group having 6 to 20 carbon atoms, and the linker may comprise at least one group selected from the group consisting of an aliphatic group having 1 to 20 carbon atoms, a heteroaliphatic group having 2 to 20 carbon atoms, an alicyclic group having 3 to 20 carbon atoms, a heteroalicyclic group having 3 to 20 carbon atoms, an aromatic group having 6 to 20 carbon atoms, and a heteroaromatic group having 6 to 20 carbon atoms, as a substituent.

In an embodiment, the ligand compound may comprise a compound represented by the following Formula 3.

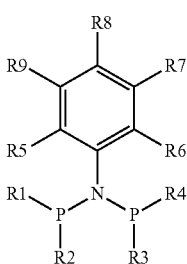

[Formula 3]

In Formula 3, R1 to R4 are the same as defined in Formula 1, and R5 is alkyl having 1 to 20 carbon atoms.

In the case that R5 is methyl, R6 may be a linear group of alkyl, alkenyl, heteroalkyl, heteroalkenyl, or a heteryl group thereof having 2 or 3 carbon atoms; alkyl, alkenyl, arylalkyl, arylalkenyl, heteroalkyl, heteroalkenyl, heteroarylalkyl, heteroarylalkenyl, or a heteryl group thereof having 4 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

In the case that R5 is alkyl having 2 to 20 carbon atoms, R6 may be alkyl, alkenyl, arylalkyl, arylalkenyl, heteroalkyl, heteroalkenyl, heteroarylalkyl, heteroarylalkenyl, or a heteryl group thereof having 2 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

R7 to R9 may be each independently hydrogen; alkyl, alkenyl, arylalkyl, or arylalkenyl having 1 to 20 carbon atoms; cycloalkyl, cycloalkenyl, arylcycloalkyl, or arylcycloalkenyl having 3 to 20 carbon atoms; aryl having 6 to 20 carbon atoms; or alkylaryl having 7 to 20 carbon atoms.

In an embodiment, the transition metal compound may comprise an organic chromium compound, and the organic chromium compound may comprise at least one selected from the group consisting of chromium(III) acetyl acetonate, trichlorochromium tris tetrahydrofuran, chromium(III)-2-ethylhexanoate, chromium(III) tris (2,2,6,6-tetramethyl-3,5-heptanedionate), chromium(III) benzoyl acetonate, chromium(III) hexafluoro-2,4-pentanedionate and chromium(III) acetate hydroxide.

In an embodiment, the co-catalyst may be at least one selected from the compounds represented by the following Formulae 4 to 6.

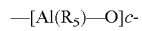

[Formula 4]

In the above Formula 4, each $R_5$ is the same or different and is independently a halogen radical, a hydrocarbyl radical having 1 to 20 carbon atoms, or a halogen substituted hydrocarbyl radical having 1 to 20 carbon atoms, and c is an integer of at least 2.

[Formula 5]

In the above Formula 5, D is aluminum or boron, each $R_6$ is the same or different and is independently hydrogen, halogen, hydrocarbyl having 1 to 20 carbon atoms, or halogen substituted hydrocarbyl having 1 to 20 carbon atoms.

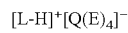

[Formula 6]

In the above Formula 6, L is a neutral Lewis base, $[L-H]^+$ is a brönsted acid, Q is boron or aluminum with an oxidation state of +3, and each E is independently aryl having 6 to 20 carbon atoms or alkyl having 1 to 20 carbon atoms, where at least one hydrogen atom is substituted with halogen, hydrocarbyl having 1 to 20 carbon atoms, an alkoxy functional group or a phenoxy functional group or unsubstituted.

In an embodiment, a pressure of the multimerization reaction may be 1 to 300 bar.

Advantageous Effects

According to the method for oligomerizing an olefin according to the present disclosure, the production ratio of 1-hexene and 1-octene may be controlled by controlling the reaction temperature during the multimerization reaction, which is different from a conventional method of controlling the production ratio of 1-hexene and 1-octene using a mixed catalyst. Accordingly, a side reaction accompanied with the use of the mixed catalyst may be decreased, and the ratio of 1-hexene and 1-octene may be controlled according to market demand or purpose by controlling only the reaction temperature even during performing a process.

MODE FOR CARRYING OUT THE INVENTION

Hereinafter, the present invention will be described in detail to assist the understanding of the present invention. The terms or words used in the present disclosure or claims should not be defined or interpreted in common or dictionary meaning, but should be interpreted as having a meaning that is consistent with their meaning in technical spirit of the present invention on the basis that the inventors may appropriately define the concept of the terms to explain the invention by their best way.

The terminology used herein is for the purpose of describing particular example embodiments only and is not intended to limit the present inventive concept. As used herein, the singular forms are intended to include the plural forms as well, unless the context clearly indicates otherwise.

It will be further understood that the terms "comprises", "comprising", etc. when used in this specification, specify the presence of stated features, numerals, steps, elements or the combination thereof, but do not preclude the presence or addition of one or more other features, numerals, steps, elements or the combination thereof.

In the present disclosure throughout, the terms "catalyst system" or "catalyst composition" means a state obtainable as a catalyst composition having activity by adding three components comprising a transition metal source, a ligand compound and a co-catalyst, or alternatively, two components having a transition metal compound and a co-catalyst simultaneously or in an optional order. The three components or the two components of the catalyst system may be added in the presence or non-presence of a solvent and a monomer, and the two terms may interchangeably be used.

The term "oligomerization" used in the present disclosure means the oligomerization of olefin. According to the number of the olefin, trimerization, or tetramerization may be referred to, and the general term thereof is multimerization. Particularly, in the present disclosure, the oligomerization means the selective preparation of 1-hexene and 1-octene which are main comonomers of LLDPE from ethylene.

In the present disclosure, a hydrocarbyl group means all compounds composed of only carbon and hydrogen, for example, alkyl, aryl, alkenyl, cycloalkyl, etc., and the hydrocarbyl group may mean both a linear chain and a branched chain unless otherwise referred to and may mean both unsubstituted and substituted type. For example, the alkyl having 1 to 20 carbon atoms may mean methyl, ethyl, propyl, isopropyl, butyl, isobutyl, pentyl, isopentyl, neopentyl, etc., and the aryl having 6 to 20 carbon atoms may mean, for example, phenyl, naphthyl, anthracenyl, etc., without limitation.

In the present disclosure, an alkylaryl group means aryl having at least one alkyl group as a substituent, and an arylalkyl group means alkyl having at least one aryl group as a substituent.

In the present disclosure, a heteroatom means N, O, S or P, and the heterohydrocarbyl may mean hydrocarbyl comprising at least one heteroatom. That is, the heteroalkyl may mean an alkyl of which one carbon is substituted with a heteroatom or may mean an alkyl comprising a heteroatom as a substituent. Heteroaryl group may mean an aromatic ring of which one carbon is substituted with a heteroatom such as pyridyl. In addition, the same may go for heteroarylakyl, heteroalkylaryl, heteroalkenylaryl, etc.

In the heterohydrocarbyl group, a linking point for functionalization is carbon, however, in "heteryl group" such as "hydrocarboheteryl group", "organoheteryl group", "heteryl group thereof", etc., the linking point for functionalization is a heteroatom.

Method for Oligomerizing an Olefin

According to an embodiment of the present disclosure, provided is a method for oligomerizing an olefin comprising performing a multimerization reaction of an olefin in the presence of an oligomerization catalyst system comprising a ligand compound, a transition metal compound and a co-catalyst by controlling a reaction temperature to a range of 50 to 150° C. so that a weight ratio of 1-hexene and 1-octene in a product comprising 1-hexene and 1-octene is a predetermined value, wherein the predetermined value of the weight ratio of 1-hexene to 1-octene in the product is selected from a range of 1:0.5 to 1:7.

In a conventional oligomerization method, in order to obtain 1-hexene and 1-octene, which are main products, to desired ratios at the same time, two kinds of appropriate catalysts for producing each compound are mixed to control the production ratio of two kinds of alpha olefins.

However, in the method for oligomerizing an olefin according to an embodiment of the present disclosure, 1-hexene and 1-octene may be produced in a desired ratio by controlling the reaction temperature by selecting the controlling method of the reaction temperature as a method for controlling the ratio of alpha olefins as main products. Accordingly, the chance of generating a side reaction due to the use of a mixed catalyst and the decrease of the activity of the catalyst may be prevented, and 1-hexene and 1-octene may be easily produced in a desired ratio by controlling only the reaction temperature, thereby markedly improving the convenience and/or economic feasibility of a process.

Particularly, the controlling range of the reaction temperature may be from 50 to 150° C., from 60 to 130° C., or from 70 to 110° C. By controlling the reaction temperature to the above temperature range, the desired weight ratio of 1-hexene and 1-octene may be determined prior to performing an oligomerization reaction and a predetermined value of 1-hexene and 1-octene may be obtained. In this case, the weight ratio of 1-hexene and 1-octene may be predetermined to a range of 1:0.5 to 1:7, or 1:0.9 to 1:6.6.

In addition, in the case that the reaction temperature is from 50 to 60° C., the weight ratio of 1-hexene and 1-octene may be in a range of about 1:2 to 1:7, and preferably, 1:3 to 1:7. In other words, in the case that the reaction temperature is controlled to about 50 to about 60° C., the production amount of 1-octene may be greater than 1-hexene. In the case that the reaction temperature is further increased, the ratio of 1-hexene may further increase. Even though the reaction temperature is greater than 80° C., the activity of the catalyst system may be maintained, and the production ratio of 1-hexene and 1-octene may be controlled by only controlling the temperature upto about 150° C.

That is, by using the catalyst system according to the present disclosure, the activity of the catalyst system may be maintained in an extensive temperature range, particularly, at a high temperature, and the ratio of 1-hexene and 1-octene may be controlled in a wide temperature range such as from 50 to 150° C. Accordingly, a linear alpha olefin mixture product having more diverse weight ratios may be prepared, and since the catalyst system maintains the activity in such a temperature range, the total amount of 1-hexene and 1-octene (that is, the selectivity of linear alpha olefins) may be maintained.

In addition, since the activity of the catalyst system is maintained in such a wide temperature range, the selectivity relative to the total amount of the product of 1-hexene and 1-octene may be maintained to 80 wt % or more in a whole reaction temperature range.

The application of the method for controlling the production ratio of 1-hexene and 1-octene by controlling the reaction temperature, to a method for oligomerizing olefin may be diverse, and practical application examples are as follows.

First, resultant values on the weight ratio of 1-hexene and 1-octene produced depending on the reaction temperature are obtained by repeating experiments, data on the average ratio of 1-hexene and 1-octene produced at a specific reaction temperature are classified, and a library is established from the classified data. For the mass production of alpha olefins, the temperature of a multimerization reaction is controlled using the library established in advance via the repeated experiments, and the predetermined production ratio of 1-hexene and 1-octene may be obtained as a desired value according to various conditions such as demand.

In addition, different from the process performed after establishing the library, a method of changing the reaction temperature from time to time after observing the ratio of 1-hexene and 1-octene produced during a process to a desired direction may be applied. Since the production ratio of 1-hexene tends to increase according to the increase of the multimerization reaction temperature, the above-described method may be practically applied for the change of the production ratio of 1-hexene and 1-octene according to the control of the reaction temperature.

The method of controlling the reaction temperature for controlling the ratio of 1-hexene and 1-octene may be applied to the method for oligomerizing olefin according to the present disclosure, and a practical application is not limited to the above-described two methods.

The method for preparing an olefin oligomer comprising the multimerization reaction of an olefin in the presence of the oligomerization catalyst system uses a catalyst system for oligomerizing an olefin, and a method of oligomerizing an olefin having improved activity and selectivity of a reaction may be provided. In this case, the olefin may comprise ethylene.

The method for oligomerizing an olefin according to the present disclosure may preferably be a homogeneous liquid phase reaction using an oligomerization catalyst system, a common apparatus and contacting technique in the presence or non-presence of an inert solvent, a slurry reaction in which a catalyst system is partially or wholly undissolved, a two phase liquid/liquid reaction, or a bulk phase reaction or a gas phase reaction in which an olefin product acts as a main medium. The homogeneous liquid phase reaction is preferable.

The oligomerization method of an olefin may be performed in an optional inert solvent which does not react with a catalyst compound and an activator. Appropriate inert solvents may comprise benzene, toluene, xylene, cumene, heptane, cyclohexane, methylcyclohexane, methylcyclopentane, hexane, pentane, butane, isobutene, etc., without limitation. In this case, the solvent may be used after removing a small amount of water or air acting as a catalyst poison by treating using a small amount of alkyl aluminum.

The oligomerization reaction of an olefin may be performed under a pressure from about 1 bar to about 300 bar, and preferably, from about 2 bar to about 150 bar.

The pressure conditions may be optimized conditions for the multimerization reaction of an olefin, and by multimerizing the olefin in the above pressure range, selectivity to desired alpha-olefins may be good, the amount of by-products may decrease, process operating efficiency may be increased, and costs may be saved.

Oligomerization Catalyst System
Ligand Compound

According to an embodiment of the present disclosure, a ligand compound may comprise a diphosphine moiety represented by the following Formula 1.

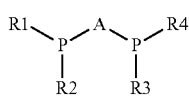

[Formula 1]

In Formula 1, A is N, As or Sb, and R1 to R4 are each independently hydrocarbyl, heterohydrocarbyl or hydrocarbylheteryl having 1 to 20 carbon atoms.

In addition, the ligand compound comprising the diphosphine moiety represented by Formula 1 may comprise at least two diphosphine moieties represented by the following Formula 2.

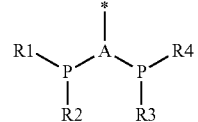

[Formula 2]

In the above Formula 2, A and R1 to R4 are the same as defined in Formula 1, and * is a linker connecting at least two diphosphine moieties.

Further, in the case that the number of the diphosphine moiety represented by the above Formula 2 is two, and A is nitrogen (N), the ligand compound may comprise a compound represented by the following Formula 2a.

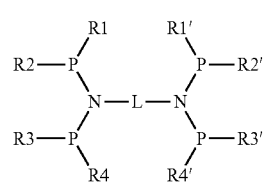

[Formula 2a]

In the above Formula 2a, each of R1 to R4 and R1' to R4' may be selected from the same group as R1 to R4 in Formula 1 or 2, and L may be a linker connecting two diphosphine moieties.

R1 to R4 in Formulae 1, 2 and 2a and R1' to R4' in Formula 2a are not specifically limited, however may be, for example, aryl, heteroaryl or arylheteryl having 6 to 20 carbon atoms; or alkylaryl, heteroalkylaryl, alkylheteroaryl or alkylarylheteryl having 7 to 20 carbon atoms. In the case that such substituents are selected, positive influences on the activity of the catalyst or the selectivity of linear alpha olefins may be obtained.

The linker L connecting at least two diphosphine moieties may be a hydrocarbyl group having various structures, and the carbon number between the diphosphine moieties for the shortest distance may be from 2 to 30. That is, the hydrocarbyl group is provided for the connection between two or more diphosphine moieties, and the carbon number in the hydrocarbyl group for connecting the diphosphine moieties with the shortest distance may be in a range of 2 to 10.

Particularly, the linker may be combined with at least one group selected from the group consisting of an aliphatic group having 2 to 20 carbon atoms, a hetero aliphatic group having 2 to 20 carbon atoms, an alicyclic group having 3 to 20 carbon atoms, a hetero alicyclic group having 3 to 20 carbon atoms, an aromatic group having 6 to 20 carbon atoms, and a hetero aromatic group having 6 to 20 carbon atoms, and may have any structure, without specific limitation only if satisfying the above conditions.

In addition, in the case that at least one group selected from the above group or a group obtained by combining at least two thereof is determined as a main chain, the main chain of the linker may have a substituent with diverse structures.

Particularly, the substituent of the linker may be at least one selected from the group consisting of an aliphatic group having 1 to 20 carbon atoms, a hetero aliphatic group having 2 to 20 carbon atoms, an alicyclic group having 3 to carbon atoms, a hetero alicyclic group having 3 to 20 carbon atoms, an aromatic group having 6 to 20 carbon atoms, and a hetero aromatic group having 6 to 20 carbon atoms. One, two or more of the substituents may be combined with the main chain, and the combining position may preferably be a far side from the diphosphine moiety in consideration of the flexibility of the linker, however the combining position of the substituent is not specifically limited thereto.

Non-limiting examples of the linker L for connecting at least two groups represented by the above Formula 1 via 2 to 30 carbon atoms may be a compound having an aliphatic group having 2 to 30 carbon atoms (for example, an alkylene group, an alkenylene group, an alkynylene group, or a hetero aliphatic group comprising a heteroatom in the aliphatic group), an alicyclic group having 2 to 20 carbon atoms (for example, a cycloalkylene group, a cycloalkenylene group, a cycloalkynylene group, or a hetero alicyclic group comprising a heteroatom in the alicyclic group), or a combined group of the aliphatic (or hetero aliphatic) group and the alicyclic (or hetero alicyclic) group.

Non-limiting examples of the linker may comprise a hydrocarbyl group represented by the following structures. In the following examples, the diphosphine moiety represented by the above Formula 1 is designated by [A], [A'] or [A"] for convenience, and [A], [A'] or [A"] may be the same or different according to the group selected for R1 to R4.

(i) a compound having a group connecting a plurality of As via two or three carbon atoms:

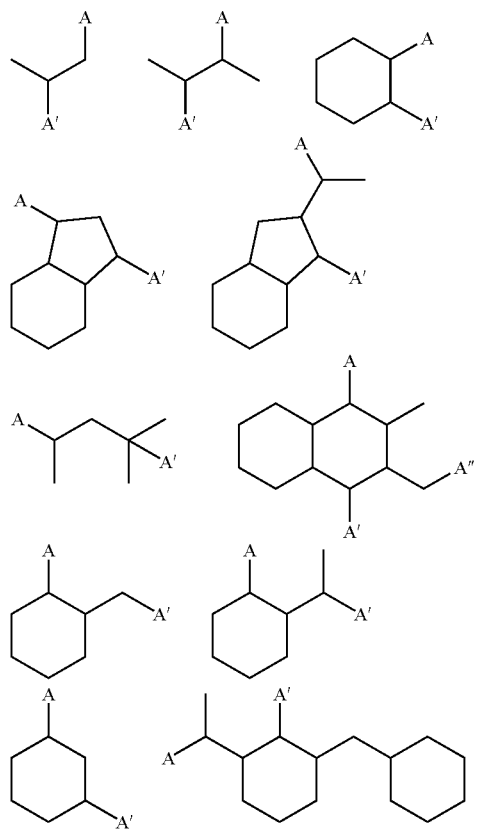

(ii) a compound having a group connecting a plurality of As via four carbon atoms:

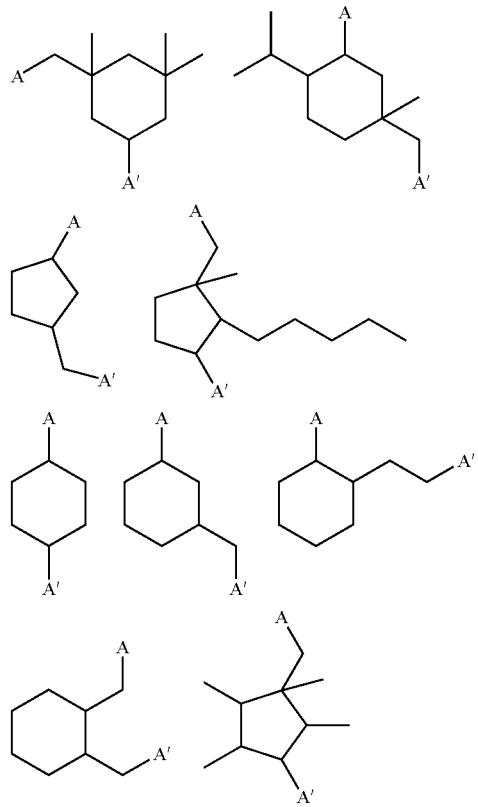

(iii) a compound having a group connecting a plurality of As via five carbon atoms:

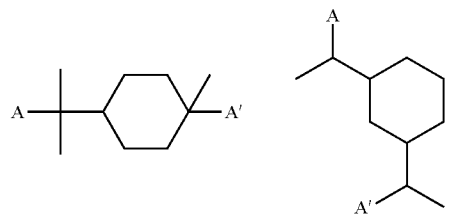

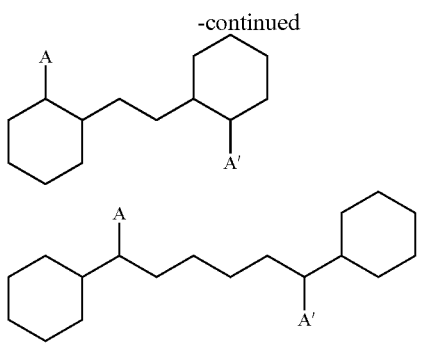

As described above, in the case that at least two diphosphine moieties represented by Formula 1 are connected via four carbon atoms, a connecting group via four carbon atoms may preferably comprise a flexible aliphatic group for favorable interaction between chromium complexes of the at least two diphosphine moieties.

That is, even though at least two diphosphine moieties represented by Formula 1 are connected via four carbon atoms, in the case that the diphosphine moieties are connected via a group not comprising an aliphatic group but only comprising an alicyclic group or an aromatic group such as cyclohexane at positions 1 and 4, interaction may be extremely limited. Accordingly, activity per unit PNP-Cr may be largely decreased, and selectivity for alpha-olefins having a small carbon number such as 1-hexene and 1-octene may be decreased.

Meanwhile, the ligand compound represented by Formula 2 or 2a may be synthesized by the following Reaction 1, without limitation.

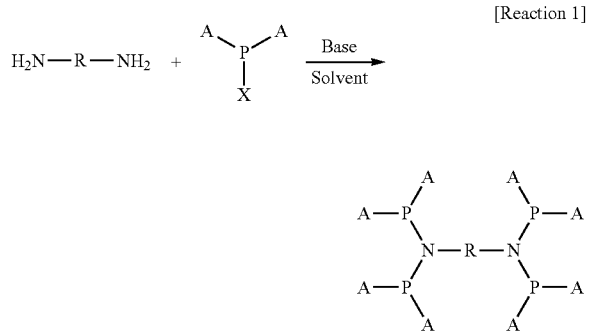

In the above Reaction 1, each A is independently the same or different from each other and is the same as defined for R1 to R4 in Formula 1, 2 or 2a, R is a linker connecting via 2 to 8 carbon atoms and the same as defined in Formula 2 or 2a, and X is halogen.

According to another embodiment of the present disclosure, the ligand compound may include a compound represented by the following Formula 3.

[Formula 3]

In Formula 3, R1 to R4 are each independently aryl having 6 to 20 carbon atoms or alkylaryl having 7 to 20 carbon atoms, and R5 is alkyl having 1 to 20 carbon atoms.

In the case that R5 is methyl, R6 may be a linear group of alkyl, alkenyl, heteroalkyl, heteroalkenyl, or a heteryl group thereof having 2 or 3 carbon atoms; alkyl, alkenyl, arylalkyl, arylalkenyl, heteroalkyl, heteroalkenyl, heteroarylalkyl, heteroarylalkenyl, or a heteryl group thereof having 4 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

In addition, in the case that R5 is methyl, R6 may preferably be heteroalkyl, heteroalkenyl, heteroarylalkyl, heteroarylalkenyl, or a heteryl group thereof having 2 to 20 carbon atoms, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

In the case that R5 is alkyl having 2 to 20 carbon atoms, R6 may be alkyl, alkenyl, arylalkyl, arylalkenyl, heteroalkyl, heteroalkenyl, heteroarylalkyl, heteroarylalkenyl, or a heteryl group thereof having 2 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

R7 to R9 may be each independently hydrogen; alkyl, alkenyl, arylalkyl, or arylalkenyl having 1 to 20 carbon atoms; cycloalkyl, cycloalkenyl, arylcycloalkyl, or arylcycloalkenyl having 3 to 20 carbon atoms; aryl having 6 to 20 carbon atoms; or alkylaryl having 7 to 20 carbon atoms.

As described above, the ligand compound represented by Formula 3 may be, for example, a compound obtained by substituting at carbon atoms of positions 2 and 6 in an aniline compound with R5 and R6, and the properties of the ligand compound and the oligomerization catalyst system comprising the same may be changed according to the substituent at the carbon atoms of positions 2 and 6.

In the case where a methyl group is substituted at the carbon atom of position 2, a group different from the substituent at position 2 may be substituted at the carbon atom of position 6 to attain an asymmetric structure.

As non-limiting examples, a linear group of an alkyl group, an alkenyl group, a heteroalkyl group, a heteroalkenyl group, or the heteryl group thereof having 2 or 3 carbon atoms may be substituted; or an alkyl group, an alkenyl group, an arylalkyl group, an arylalkenyl group, a heteroalkyl group, a heteroalkenyl group, a heteroarylalkyl group, a heteroarylalkenyl group, or the heteryl group thereof having 4 to 20 carbon atoms may be substituted.

In addition, a cycloalkyl group, a cycloalkenyl group, an arylcycloalkyl group, an arylcycloalkenyl group, a heterocycloalkyl group, a heterocycloalkenyl group, a heteroarylcycloalkyl group, a heteroarylcycloalkenyl group, or the heteryl group thereof having 3 to 20 carbon atoms may be substituted; an aryl group, a heteroaryl group, or the heteryl group thereof having 6 to 20 carbon atoms may be substituted; or an alkylaryl group, a heteroalkylaryl group, or the heteryl group thereof having 7 to 20 carbon atoms may be substituted.

In addition, in the case where an alkyl group having 2 to 20 carbon atoms is substituted at the carbon atom of position 2, a substituent same as or different from the substituent at position 2 may be substituted at the carbon atom of position 6.

As non-limiting examples, an alkyl group, an alkenyl group, an arylalkyl group, an arylalkenyl group, a heteroalkyl group, a heteroalkenyl group, a heteroarylalkyl group, a heteroarylalkenyl group, or the heteryl group thereof having 2 to 20 carbon atoms may be substituted; a cycloalkyl group, a cycloalkenyl group, an arylcycloalkyl group, an arylcycloalkenyl group, a heterocycloalkyl group, a heterocycloalkenyl group, a heteroarylcycloalkyl group, a heteroarylcycloalkenyl group, or the heteryl group thereof having 3 to 20 carbon atoms may be substituted; an aryl group, a heteroaryl group, or the heteryl group thereof having 6 to 20 carbon atoms may be substituted; or an alkylaryl group, a heteroalkylaryl group, or the heteryl group thereof having 7 to 20 carbon atoms may be substituted.

Due to the structural characteristics of the substituent groups for the aniline group, in the catalyst system comprising the ligand compound, PNP-Cr may easily interact according to various conditions such as electronic or steric circumstances around a transition metal, and the high activity of an oligomerization reaction may be illustrated. Particularly, high selectivity particularly for 1-hexene, 1-octene, etc. may be illustrated, and incidentally, energy may be saved, because a separating process may become unnecessary according to the increase of 1-hexene and the decrease of an 1-hexene isomer.

The ligand compound may be synthesized by the following Reaction 2, without limitation.

[Reaction 2]

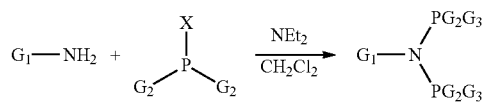

In the above Reaction 2, G1 may be a phenyl group having R5 to R9 in Formula 3, each of G2 and G3 may be R1 to R4 in Formula 3, and X may be halogen.

Reaction 2 is a general reaction for synthesizing a ligand compound represented by Formula 3 and may be a reaction for producing diphosphinoamine via the reaction of an amine and phosphine. That is, in the reaction, the amine as a nucleophile may push a leaving group represented by X in the phosphine for substitution. X may be any functional group which may be easily separated and stabilized, without limitation. Typically, halogens such as Cl, Br or I may be used.

Ligand Compound and Transition Metal Compound

Such a selective olefin oligomerization reaction is closely concerned with a catalyst system used. The catalyst system used for the oligomerization reaction of an olefin comprises a transition metal compound functioning as a main catalyst and a co-catalyst. In this case, according to the chemical structure of the ligand, the structure of an active catalyst may be changed, and so, olefin selectivity, activity or the amount of by-products may be changed.

The transition metal compound in the oligomerization catalyst system according to an embodiment of the present disclosure acts as a main catalyst and may have a state making a coordination bond with the ligand compound as described above.

Particularly, the transition metal and the ligand compound comprising at least two diphosphine moieties represented by the above Formula 2 may make a coordination bond as represented in the following Formula 2-1.

[Formula 2-1]

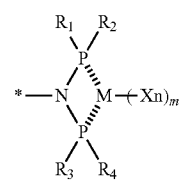

In the above Formula 2-1, R1 to R4 are the same as defined in Formula 1 and is the same as defined in Formula 2, M may be a transition metal, and preferably, Cr, Xn may be H, F, Cl, Br, I, alkyl, alkenyl, arylalkyl, heteroalkyl, heteroalkenyl or heteroarylalkyl having 1 to 6 carbon atoms, halogen, acetate, or acetyl acetonate, and m is an oxidation number of M and may be a natural number.

In addition, the transition metal compound and the ligand compound represented by Formula 2a may make a coordination bond as shown in the following Formula 2a-1.

[Formula 2a-1]

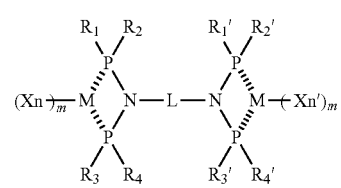

In Formula 2a-1, R1 to R4, Xn, m and M are the same as defined in Formula 2-1, and R1' to R4' and Xn' are also the same as R1 to R4 and X1 to X3.

In addition, the transition metal compound and the ligand compound represented by Formula 3 may make a coordination bond as shown in the following Formula 3-1.

[Formula 3-1]

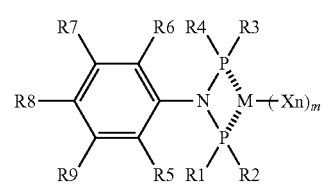

In Formula 3-1, Xn, m and M are the same as defined in Formula 2-1, and R1 to R9 are the same as defined in Formula 3.

Particularly, the transition metal compound may comprise an organochromium compound, and the organochromium compound may be at least one selected from the group consisting of chromium(III)acetylacetonate, trichlorochromiumtristetrahydrofuran, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate and chromium(III)acetatehydroxide.

Co-Catalyst

The co-catalyst is an organometallic compound comprising a metal in group 13 and may be generally any one which may be used for multimerizing an olefin in the presence of a transition metal compound catalyst, without specific limitation. Particularly, the co-catalyst may be at least one selected from the group consisting of the compounds represented by the following Formulae 4 to 6.

—[Al($R_5$)—O]$c$-  [Formula 4]

In the above Formula 4, each $R_5$ is the same or different from each other and is independently a halogen radical, a hydrocarbyl radical having 1 to 20 carbon atoms, or a halogen substituted hydrocarbyl radical having 1 to 20 carbon atoms, and c is an integer of at least 2.

D($R_6$)$_3$  [Formula 5]

In the above Formula 5, D is aluminum or boron, each $R_6$ is the same or different from each other and is independently hydrogen or halogen, a hydrocarbyl having 1 to 20 carbon atoms, or halogen substituted hydrocarbyl having 1 to 20 carbon atoms.

[L-H]$^+$[Q(E)$_4$]$^-$  [Formula 6]

In the above Formula 6, L is a neutral Lewis base, [L-H]$^+$ is a brönsted acid, Q is boron or aluminum with an oxidation state of +3, and each E is independently aryl having 6 to 20 carbon atoms or alkyl having 1 to 20 carbon atoms, where at least one hydrogen atom is substituted with halogen, hydrocarbyl having 1 to 20 carbon atoms, an alkoxy functional group or a phenoxy functional group or unsubstituted.

The compound represented by Formula 4 may be modified methyl aluminoxane (MAO), methyl aluminoxane (MAO), ethyl aluminoxane, isobutyl aluminoxane, butyl aluminoxane, etc.

The alkyl metal compound represented by the above Formula 5 may comprise, for example, trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc.

Examples of the compound represented by the above Formula 6 comprises, for example, triethylammoniumtetraphenylboron, tributylammoniumtetraphenylboron, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylanilinumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentafluorophenylaluminum, triphenylphosphoniumtetraphenylaluminum, trimethylphosphoniumtetraphenylaluminum, triphenylcarboniumtetraphenylboron, triphenylcarboniumtetraphenylaluminum, triphenylcarboniumtetra(p-trifluoromethylphenyl)boron, triphenylcarboniumtetrapentafluorophenylboron, etc.

The co-catalyst of the oligomerization catalyst system according to an embodiment may preferably comprise aluminoxane, and more preferably, methyl aluminoxane (MAO) or modified methyl aluminoxane (MMAO) may be used.

Method for Preparing Oligomerization Catalyst System

Non-limiting examples of the method for preparing the oligomerization catalyst system may comprise a step of preparing a catalyst composition by mixing the ligand compound and a transition metal compound; and a step of mixing and activating a co-catalyst and the catalyst composition at a temperature of −40 to 80° C.

The catalyst composition comprises the ligand compound and the transition metal compound, and according to the method for preparing the oligomerization catalyst system according to the present disclosure, the ligand compound and the transition metal compound are mixed in advance to induce a metalation reaction between the two compounds.

The metalation reaction may be a reaction for making a coordination bond between the ligand compound and the transition metal compound, and the coordination state of the ligand compound and the transition metal compound, the activation point of the ligand compound, etc. will be explained below.

After a catalyst composition is prepared via a sufficient metalation reaction of the ligand compound and the transition metal compound, the catalyst composition and a co-catalyst are mixed and activated. The activation may mean activation as an oligomerization catalyst system via the contact and aging of the catalyst composition and the co-catalyst.

The activation of the catalyst composition and the co-catalyst may be performed by contacting the co-catalyst and the catalyst composition present as a liquid phase after being mixed with an organic solvent, and aging for a certain time period. The activation may be performed by stirring, simple mixing, etc., without specific limitation, and any method for generating the activity as the oligomerization catalyst system via the contact of the catalyst composition and the co-catalyst may be applied.

The organic solvent may comprise, for example, heptane, toluene, cyclohexane, methylcyclohexane, 1-hexene, diethyl ether, tetrahydrofuran, acetonitrile, dichloromethane, chloroform, chlorobenzene, methanol, acetone, etc., without limitation.

The activation of the catalyst composition and the co-catalyst may be performed at a temperature from −40 to 80° C., and preferably, from 20 to 80° C. or from 25 to 60° C. In the case that the contact and aging of the catalyst composition with the co-catalyst for activation is performed at a high temperature greater than 80° C., the ligand and the transition metal of the catalyst composition may be excessively activated by a metal alkyl possibly used as the co-catalyst, and by-products may be produced during an oligomerization reaction or the activity may be decreased at an early stage.

In addition, in the case that the contact and aging of the catalyst composition with the co-catalyst for activation is performed at an extremely low temperature less than −40° C., energy necessary for the activation of a catalyst may not be supplied, and the catalyst may not be activated.

The activation of the catalyst composition and the co-catalyst may be the contact of the co-catalyst and the catalyst composition present as a liquid phase after being mixed with an organic solvent, and aging for a certain time period. The activation may be performed by stirring, simple mixing, etc., without specific limitation, and any method for producing the activity as the oligomerization catalyst system via the contact of the catalyst composition and the co-catalyst may be applied.

The organic solvent may comprise, for example, heptane, toluene, cyclohexane, methylcyclohexane, 1-hexene, diethyl ether, tetrahydrofuran, acetonitrile, dichloromethane, chloroform, chlorobenzene, methanol, acetone, etc., without limitation.

For example, in the case that time necessary from an initial contact point of the co-catalyst and the catalyst composition (the temperature at this point is referred to as "temperature a") to a point just before the contact with a reactant (for example, ethylene) is set to time A, and time necessary for elevating the temperature of a mixture of the catalyst composition, the co-catalyst and the reactant to an oligomerization temperature (the reaction temperature is referred to as "temperature b") is set to time B, the activation time of the co-catalyst and the catalyst composition may mean the sum of time A and time B, or in the case that the initial point of time A and the initial point of time B are different, and firstly initiated time is firstly over, may mean time consumed from the initial point of the firstly initiated time to the end point of a subsequently initiated time. Alternatively, in the case where one time is included in another time consumed for a longer period (for example, in the case that time A is completely included in time B, or time B is completely included in time A), the activation time may mean longer time.

The activation of the catalyst composition and the co-catalyst may be performed within five minutes, and preferably, in three minutes. In the case that the contact and aging time of the catalyst composition and the co-catalyst for the activation is greater than five minutes, the over-activation of the oligomerization catalyst system may occur as in the case that the activation is performed at a high temperature, and the time may preferably be within five minutes.

In the method for preparing an oligomerization catalyst system according to an embodiment of the present disclosure, when the activation is attained at a low temperature in a short time as the activation conditions of the catalyst composition and the co-catalyst, the coordination bond of the ligand compound and the transition metal compound of the oligomerization catalyst system may be stabilized, and the thermostability of the catalyst system may increase. In this case, even though an oligomerization reaction is performed at a high temperature (from about 60° C. to about 120° C.), the catalyst system has high structural durability and little changes in physical properties, and the activity of the catalyst system may be continuously maintained.

The activity of the catalyst system manufactured in the above-described activation conditions may be about 100,000 kg/molCr/hr or more in a batch type process, preferably, may be 120,000 kg/molCr/hr or more, and more preferably, 150,000 kg/molCr/hr or more. In addition, the activity of the catalyst system may be about 100,000 kg/molCr or more in a continuous type process, preferably, 120,000 kg/molCr or more, and more preferably, 150,000 kg/molCr or more. The activity of the catalyst system may not be decreased but maintained at a high temperature as described above, and an activation decrease ratio according to the increase of the oligomerization reaction temperature may be less than 6%. In this case, the oligomerization reaction temperature may be in a range of 30 to 150° C., 60 to 130° C., or 70 to 110° C.

Meanwhile, generally, in the case where an oligomerization process is a batch type process, the co-catalyst may be mixed in an organic solvent phase and injected to a reactor, and the catalyst composition may be injected together with an olefin which is a reactant, directly injected to the reactor, or injected to a line for injecting the co-catalyst and injected to the reactor. In addition, in the case where the oligomerization process is a continuous type process, the co-catalyst and the catalyst composition may be injected to the reactor via separate lines, and the reactant may be also injected via a separate line to the reactor. Accordingly, with the decrease of contact time with the reactor, the activity may be possibly maintained at a high temperature.

In the oligomerization catalyst system, the molar ratio of the ligand compound:transition metal compound:co-catalyst may be from about 0.5:1:1 to about 10:1:10,000, and preferably, from about 0.5:1:100 to about 5:1:3,000 to increase selectivity to linear alpha olefins and the activity of a multimerization reaction. However, an example of the oligomerization catalyst system according to the present disclosure is not limited thereto.

EXAMPLES

Hereinafter, examples of the present invention will be explained in detail so that a person skilled in the art may easily perform. However, the present invention may be embodied in various modifications and is not limited to the examples herein.

<Synthesis of the Ligand Compound>

All reactions were performed under an argon atmosphere using Schlenk technique or a glove box. The ligand synthesized was analyzed after taking $^1$H (500 MHz) and P (202 MHz) NMR spectra using a Varian 500 MHz spectrometer. Chemical shift values were represented by ppm downfield from TMS with a residual solvent peak as a reference. A phosphorous probe was calibrated using aqueous $H_3PO_4$.

Preparation Example

Under an argon atmosphere, 3-(aminomethyl)-3,5,5-trimethylcyclohexaneamine (5 mmol) and triethylamine (3-10 eq. to amine) were dissolved in dichloromethane (80 ml). With a flask in a water bath, chloroditolylphosphine (20 mmol, 2 eq. to amine) was slowly added and stirred overnight. After evaporating solvents in vacuum, THF was added and sufficiently stirred. A triethylammonium chloride salt was removed using an air-free glass filter. Solvents were removed from the filtrate to obtain a product.

Preparation of the Alpha-Olefin Oligomer

Examples 1 to 5

(Step 1)

Under an argon gas atmosphere, Cr(acac)$_3$ (17.5 mg, 0.014 mmol) and a ligand compound (1.1 eq. to Cr) prepared according to the preparation example were added to a flask, and 100 ml of methylcyclohexane was added thereto, followed by stirring to obtain a 0.5 mM (to Cr) solution.

(Step 2)

A parr reactor having a volume of 600 ml was prepared and a vacuum state was made at 180° C. for 2 hours. Then, the inner portion of the reactor was replaced with argon and the temperature was decreased to 60° C. 140 g of methylcyclohexane and 1.6 ml of MMAO (8.6 wt %, isoheptane solution) (Al/Cr=1,200) were injected to the reactor, and 5 ml (2.5 µmol) of the 0.5 mM solution was injected to the reactor. The valve of an ethylene line adjusted to 60 bar was opened to fill up the reactor with ethylene, followed by stirring at a temperature range of 70 to 110° C. while changing the temperature by the unit of 10° C. (each for Examples 1 to 5) in 500 rpm for 15 minutes at each temperature.

The valve of an ethylene line was closed, and the reactor was cooled to 0° C. using a dry ice/acetone bath, unreacted ethylene was slowly ventilated, and 1 ml of nonane (GC internal standard) was injected. After that, a small amount of the liquid portion of the reactor was collected and quenched with water. An organic layer was filtered using a PTFE syringe filter, and GC analysis was conducted.

(Step 3)

400 ml of ethanol/HCl (10 vol %) was added to the remaining reaction product, followed by stirring and filtering to obtain a polymer. The polymer thus obtained was dried at 60° C. in a vacuum oven overnight, and the weight was measured.

Experimental Example 1: Oligomerization Reaction According to the Control of Reaction Temperature The results of Examples 1 to 5 are shown in the following Table 1.

TABLE 1

| | Reaction temperature ° C. | Activity kg/molCr/hr | 1-C6 wt % | 1-C8 wt % | 1-C6 + 1-C8 wt % |
|---|---|---|---|---|---|
| Example 1 | 70 | 141,155 | 26 | 62 | 88 |
| Example 2 | 80 | 133,684 | 28 | 57 | 85 |
| Example 3 | 90 | 145,191 | 31 | 54 | 85 |
| Example 4 | 100 | 195,526 | 39 | 45 | 84 |
| Example 5 | 110 | 177,405 | 45 | 39 | 84 |

Referring to Table 1, the reaction was performed with the reaction temperature for the oligomerization of 70° C. in Example 1, and the ratio of 1-hexene and 1-octene was about 1:3. By performing the reaction while slowly increasing the reaction temperature from 70° C. to 110° C., the production ratio of 1-hexene and 1-octene was changed with tendency, and the weight ratio of 1-hexene and 1-octene was gradually changed from about 1:3 to about 1:0.9.

Conventionally, since the production ratio of 1 hexene and 1-octene was controlled via the mixing ratio of a catalyst for preparing 1-hexene and a catalyst for preparing 1-octene, the production ratio may not be easily changed during factory operation, by-products may be produced due to interaction between catalysts, or activation decrease or over-activation may be generated. However, according to the oligomerization method provided by the present disclosure, the production ratio of 1-hexene and 1-octene may be simply controlled by controlling only the reaction temperature of oligomerization. The temperature control may be performed during factory operation or at initial setting, and there are quite a lot of merits.

Example 6

Preparation of the Oligomerization Catalyst System

Under an argon gas atmosphere, Cr(acac)$_3$ (17.5 mg, 0.014 mmol) and the ligand compound (1.1 eq. to Cr) prepared according to the preparation method were added to a flask, and 100 ml of methylcyclohexane was added thereto, followed by stirring to obtain a 0.5 mM (to Cr) catalyst composition.

Then, 32 ml of MMAO (8.6 wt %, isoheptane solution) (Al/Cr=1,200) and 100 ml of the 0.5 mM catalyst composition were premixed in a round-bottomed flask for 2 minutes to prepare an oligomerization catalyst system.

Oligomerization of an Olefin

A parr reactor having a volume of 600 ml was prepared and a vacuum state was made at 180° C. for 2 hours. Then, the inner portion of the reactor was replaced with argon, and the temperature was decreased to a reaction temperature of 60° C. 140 g of methylcyclohexane was injected to the reactor, and 6.6 ml (2.5 µmol) of the premixed solution (oligomerization catalyst system) was injected to the reactor Immediately after the injection, the valve of an ethylene line adjusted to 60 bar was opened to fill up the reactor with ethylene, followed by stirring at the reaction temperature of 60° C. in 500 rpm for 15 minutes.

The valve of an ethylene line was closed, and the reactor was cooled to 0° C. using a dry ice/acetone bath, unreacted ethylene was slowly ventilated, and 1 ml of nonane (GC internal standard) was injected. After that, a small amount of the liquid portion of the reactor was collected and quenched with water. An organic layer was filtered using a PTFE syringe filter, and GC analysis was conducted.

400 ml of ethanol/HCl (10 vol %) was added to the remaining reaction product, followed by stirring and filtering to obtain a polymer. The polymer thus obtained was dried at 60° C. in a vacuum oven overnight, and the weight was measured.

Example 7

The preparation of a catalyst system, oligomerization, GC analysis and the measurement of the weight of the polymer thus obtained were performed according to the same method described in Example 1 except for setting the activation temperature to 60° C. during premixing for preparing the oligomerization catalyst system.

Example 8

The preparation of a catalyst system, oligomerization, GC analysis and the measurement of the weight of a polymer thus obtained were performed according to the same method described in Example 1 except for setting the oligomerization reaction temperature to 80° C.

Example 9

The preparation of a catalyst system, oligomerization, GC analysis and the measurement of the weight of the polymer thus obtained were performed according to the same method described in Example 1 except for setting the activation temperature to 80° C. and the oligomerization reaction temperature to 80° C. during premixing for preparing the oligomerization catalyst system.

Comparative Examples 1 to 4

The preparation of a catalyst system, oligomerization, GC analysis and the measurement of the weight of the polymers thus obtained were performed according to the same method described in Example 1 except for setting the mixing time and activation temperature during premixing for preparing the oligomerization catalyst system and the oligomerization temperature as in the following Table 2.

Experimental Example 2: Oligomerization Reaction According to Catalyst Activation Conditions The results of Examples 6 to 9 and Comparative Examples 1 to 4 are shown in the following Table 2.

TABLE 2

| | Premixing | | Reaction | | | | | 1-C6 + |
|---|---|---|---|---|---|---|---|---|
| | Temperature (° C.) | Time (min) | temperature ° C. | T ° C. | Activity Ton/molCr/hr | 1-C6 % | 1-C8 % | 1-C8 % |
| Example 6 | 25 | 2 | 60 | 40 | 182 | 41.8 | 43.6 | 90.6 |
| Example 7 | 60 | 2 | 60 | 13 | 175 | 47.3 | 42.0 | 89.3 |
| Example 8 | 25 | 2 | 80 | 15 | 174 | 47.1 | 43.6 | 90.6 |
| Example 9 | 80 | 2 | 80 | 13 | 157 | 47.0 | 43.3 | 90.3 |
| Comparative Example 1 | 25 | 100 | 60 | 4 | 50 | 24.1 | 65.4 | 89.5 |
| Comparative Example 2 | 25 | 5 | 80 | 0 | 42 | 30.3 | 54.6 | 85.0 |
| Comparative Example 3 | 80 | 5 | 80 | 4 | 44 | 40.3 | 50.0 | 90.3 |
| Comparative Example 4 | 80 | 100 | 80 | 0 | 0 | 0 | 0 | 0 |

Referring to Table 2, the activity of the catalyst systems obtained in Examples 1 to 4 by aging the co-catalyst and the catalyst composition at the temperature of −40 to 80° C. with the aging time of less than five minutes was markedly better when compared to those of Comparative Examples 1 to 4 obtained by aging for five minutes or more. That is, the activating conditions of the catalyst composition and the co-catalyst included the temperature of −40 to 80° C. with the short aging time of less than five minutes.

Example 10

Under a nitrogen gas atmosphere, cyclohexane and ethylene were continuously injected with the flow rate of 1.2 kg/hr and 1.75 kg/hr to a 2 L CSTR reactor, and the pressure was maintained to 60 bar. To a 10 L pressurized vessel, the ligand prepared in the preparation example and Cr(acac)$_3$ were injected in a molar ratio of 0.55:1, and a catalyst solution diluted in cyclohexane to 0.05 M was injected with a rate of 5.8 ml/min, and at the same time, a solution of MMAO co-catalyst diluted in cyclohexane was continuously injected in line with the amount injected of the catalyst solution so that the molar ratio of Al:Cr was 1,200:1. The reaction temperature was controlled to 60° C. by continuously injecting water at room temperature to a reactor jacket. During performing a stable reaction for 2 hours, a reaction product drained was collected for 1 hour and 5 ml thereof was taken and quenched with water. An organic layer was filtered using a PTFE syringe filter, GC analysis was conducted.

Experimental Example 3: Oligomerization Reaction According to Catalyst Activation Conditions (Continuous Process)

The results of Example 10 are shown in the following Table 3.

TABLE 3

| | Activity kg/molCr | 1-C6 wt % | 1-C8 wt % | 1-C6 + 1-C8 wt % | 1-C10 to 1-C40 wt % | C6 isomer wt % |
|---|---|---|---|---|---|---|
| Example 10 | 128,900 | 32.5 | 53.4 | 85.8 | 11.6 | 1.8 |

Referring to Table 3, good activity of a catalyst system may be obtained even though applying the activation step of a catalyst system according to the present disclosure to a continuous process as in Example 10, like in the batch type process of Examples 6 to 9. Accordingly, the activity of the catalyst system may be good as in the batch type process, and the selectivity of linear alpha olefins may be also good.

While this invention has been particularly shown and described with reference to preferred embodiments thereof and drawings, it will be understood by those skilled in the art that various changes in form and details may be made therein without departing from the spirit and scope of the invention as defined by the appended claims.

The invention claimed is:

1. A method for oligomerizing an olefin, the method comprising:
    performing a multimerization reaction of an olefin in the presence of an oligomerization catalyst system comprising a ligand compound, a transition metal compound, and a co-catalyst, and
    controlling a reaction temperature during the multimerization reaction in a range of 30 to 150° C., such that a product of the multimerization reaction comprising 1-hexene and 1-octene has a predetermined value of a weight ratio of 1-hexene and 1-octene selected from a range of 1:0.5 to 1:7, wherein the olefin comprises ethylene, wherein the transition metal compound comprises an organic chromium compound, and wherein the oligomerization catalyst system is prepared by preparing a catalyst composition by mixing the ligand compound and the transition metal compound, and activated by mixing a co-catalyst and the catalyst composition for less than five minutes at a temperature of 25 to 80° C.

2. The method for oligomerizing an olefin of claim 1, wherein the predetermined value of the weight ratio is from 1:0.9 to 1:6.6.

3. The method for oligomerizing an olefin of claim 1, wherein the reaction temperature is controlled in a range of 60 to 130° C.

4. The method for oligomerizing an olefin of claim 1, wherein a weight ratio of 1-hexene in relation to 1-octene in the product increases when the reaction temperature is increased.

5. The method for oligomerizing an olefin of claim 1, wherein a selectivity of 1-hexene and 1-octene relative to a total amount of the product is 80 wt % or more in the whole reaction temperature range.

6. The method for oligomerizing an olefin of claim 1, wherein an activity of the oligomerization catalyst system decreases 9% or less in the whole reaction temperature range when the reaction temperature is increased.

7. The method for oligomerizing an olefin of claim 1, wherein an activity of the oligomerization catalyst system in the whole reaction temperature range is 100,000 kg/molCr/hr or more in a batch process, and 100,000 kg/molCr/hr or more in a continuous process.

8. The method for oligomerizing an olefin of claim 1, wherein an activating time of the co-catalyst and the catalyst composition is three minutes or less.

9. The method for oligomerizing an olefin of claim 1, wherein the ligand compound comprises a diphosphine moiety represented by the following Formula 1:

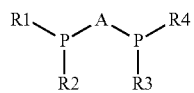

[Formula 1]

wherein in Formula 1, A is N, As or Sb, R1 to R4 are each independently a hydrocarbyl group, a heterohydrocarbyl group, or a hydrocarbylheteryl group, each group having 1 to 20 carbon atoms.

10. The method for oligomerizing an olefin of claim 9, wherein the ligand compound comprises at least two diphosphine moieties represented by the following Formula 2, and a hydrocarbyl linker connecting the at least two diphosphine moieties and having a carbon number of the shortest distance between the diphosphine moieties of from 2 to 30:

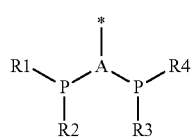

[Formula 2]

wherein in Formula 2, A and R1 to R4 are the same as defined in Formula 1, and * is the hydrocarbyl linker connecting the at least two diphosphine moieties.

11. The method for oligomerizing an olefin of claim 10, wherein the hydrocarbyl linker comprises at least one group selected from the group consisting of an aliphatic group having 1 to 20 carbon atoms, an alicyclic group having 3 to 20 carbon atoms, an aromatic group having 6 to 20 carbon atoms, and a combination thereof.

12. The method for oligomerizing an olefin of claim 9, wherein the ligand compound is represented by the following Formula 3:

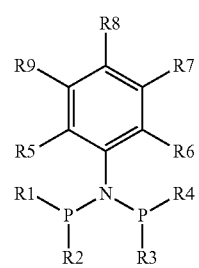

[Formula 3]

wherein in Formula 3,

R1 to R4 are the same as defined in Formula 1,

R5 is an alkyl group having 1 to 20 carbon atoms, wherein in the case that R5 is a methyl group, R6 is a linear C2-C3 alkyl group, a linear C2-C3 alkenyl group, a linear C2-C3 heteroalkyl group, a linear C2-C3 heteroalkenyl group, or a C2-C3 heteryl group thereof; a C4-C20 alkyl group, a C4-C20 alkenyl group, a C4-C20 arylalkyl group, a C4-C20 arylalkenyl group, a C4-C20 heteroalkyl group, a C4-C20 heteroalkenyl group, a C4-C20 heteroarylalkyl group, a C4-C20 heteroarylalkenyl group, or a C4-C20 heteryl group thereof; a C3-C20 cycloalkyl group, a C3-C20 cycloalkenyl group, a C3-C20 arylcycloalkyl group, a C3-C20 arylcycloalkenyl group, a C3-C20 heterocycloalkyl group, a C3-C20 heterocycloalkenyl group, a C3-C20 heteroarylcycloalkyl group, a C3-C20 heteroarylcycloalkenyl group, or a C3-C20 heteryl group thereof; a C6-C20 aryl group, a C6-C20 heteroaryl group, or a C6-C20 heteryl group thereof; or a C7-C20 alkylaryl group, a C7-C20 heteroalkylaryl group, or a C7-C20 heteryl group thereof;

wherein in the case that R5 is an alkyl group having 2 to 20 carbon atoms, R6 is a C2-C20 alkyl group, a C2-C20 alkenyl group, a C2-C20 arylalkyl group, a C2-C20 arylalkenyl group, a C2-C20 heteroalkyl group, a C2-C20 heteroalkenyl group, a C2-C20 heteroarylalkyl group, a C2-C20 heteroarylalkenyl group, or a C2-C20 heteryl group thereof; a C3-C20 cycloalkyl group, a C3-C20 cycloalkenyl group, a C3-C20 arylcycloalkyl group, a C3-C20 arylcycloalkenyl group, a C3-C20 heterocycloalkyl group, a C3-C20 heterocycloalkenyl group, a C3-C20 heteroarylcycloalkyl group, a C3-C20 heteroarylcycloalkenyl group, or a C3-C20 heteryl group thereof; a C6-C20 aryl group, a C6-C20 heteroaryl group, or a C6-C20 heteryl group thereof; or a C7-C20 alkylaryl group, a C7-C20 heteroalkylaryl group, or a C7-C20 heteryl group thereof; and R7 to R9 are each independently hydrogen; a C1-C20 alkyl group, a C1-C20 alkenyl group, a C1-C20 arylalkyl group, or a C1-C20 arylalkenyl group; a C3-C20 cycloalkyl group, a C3-C20 cycloalkenyl group, a C3-C20 arylcycloalkyl group, or a C3-C20 arylcycloalkenyl group; a C6-C20 aryl group; or a C7-C20 alkylaryl group.

13. The method for oligomerizing an olefin of claim 12, wherein R7 to R9 of Formula 3 are hydrogen.

14. The method for oligomerizing an olefin of claim 1, wherein the organic chromium compound is selected from the group consisting of chromium(III) acetyl acetonate, trichlorochromium tris(tetrahydrofuran), chromium(III)-2-ethylhexanoate, chromium(III) tris (2,2,6,6-tetramethyl-3,5-heptanedionate), chromium(III) benzoyl acetonate, chromium(III) hexafluoro-2,4-pentanedionate, and chromium(III) acetate hydroxide.

15. The method for oligomerizing an olefin of claim 1, wherein the co-catalyst is at least one selected from compounds represented by the following Formulae 4 to 6:

—[Al($R_5$)—O]$c$-   [Formula 4]

wherein in the above Formula 4, each R5 is the same or different and is independently a halogen radical, a hydrocarbyl radical having 1 to 20 carbon atoms, or a halogen substituted hydrocarbyl radical having 1 to 20 carbon atoms, and c is an integer of at least 2;

D($R_6$)$_3$   [Formula 5]

wherein in the above Formula 5, D is aluminum or boron, each $R_6$ is the same or different and is independently a hydrogen, a halogen, a hydrocarbyl group having 1 to 20 carbon atoms, or a halogen substituted hydrocarbyl group having 1 to 20 carbon atoms;

[L-H]$^+$[Q(E)$_4$]$^-$   [Formula 6]

wherein in the above Formula 6, L is a neutral Lewis base, [L-H]$^+$ is a Brönsted acid, Q is boron or aluminum with an oxidation state of +3, and each E is independently an aryl group having 6 to 20 carbon atoms or an alkyl group having 1 to 20 carbon atoms, where at least one hydrogen atom is optionally substituted with a halogen, a C1-C20 hydrocarbyl group, an alkoxy functional group or a phenoxy functional group.

16. The method for oligomerizing an olefin of claim 1, wherein a pressure of the multimerization reaction is 1 to 300 bar.

* * * * *